United States Patent
Wu et al.

(10) Patent No.: US 10,865,405 B2
(45) Date of Patent: Dec. 15, 2020

(54) MALTOOLIGOSYL TREHALOSE SYNTHASE MUTANT WITH IMPROVED THERMAL STABILITY

(71) Applicant: Jiangnan University, Wuxi (CN)

(72) Inventors: Jing Wu, Wuxi (CN); Lingqia Su, Wuxi (CN); Chun Chen, Wuxi (CN); Zirui Wang, Wuxi (CN); Jinyun Feng, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 16/426,120

(22) Filed: May 30, 2019

(65) Prior Publication Data

US 2019/0367899 A1   Dec. 5, 2019

(30) Foreign Application Priority Data

Jun. 5, 2018 (CN) .......................... 2018 1 0568782
Apr. 19, 2019 (CN) .......................... 2019 1 0318019

(51) Int. Cl.
   *C12N 9/90* (2006.01)
   *C12P 19/12* (2006.01)
   *C12P 19/24* (2006.01)

(52) U.S. Cl.
   CPC ............... *C12N 9/90* (2013.01); *C12P 19/12* (2013.01); *C12P 19/24* (2013.01); *C12Y 504/99015* (2013.01)

(58) Field of Classification Search
   None
   See application file for complete search history.

(56) References Cited

PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Fang et al. J Agric Food Chem. Jul. 11, 2007;55(14):5588-94. Epub Jun. 14, 2007 (Year: 2007).*
Yang et al. J. Agric. Food Chem. 2016, 64, 40, 7546-7554 (Year: 2016).*
Li et al. Biotechnol Bioeng. Jul. 2014;111(7):1273-87. Epub May 6, 2014. (Year: 2014).*
Accession Q9AJN7. Jun. 1, 2001 (Year: 2001).*

* cited by examiner

*Primary Examiner* — Christian L Fronda
(74) *Attorney, Agent, or Firm* — IPro, PLLC

(57) ABSTRACT

The present disclosure discloses a maltooligosyl trehalose synthase mutant with improved thermal stability, and belongs to the technical fields of enzyme engineering and protein engineering. The residual enzyme activities of the MTSase mutants S361R, S444E, S361R/S444E, S361K/S444E, G415P/S361R/S444E and G415P consistent with the present disclosure after treatment at 60° C. for 10 min are respectively 70.3%, 50.1%, 83.5%, 65.9%, 100% and 80.7%, which are respectively 1.6, 1.1, 1.9, 1.5, 2.3 and 1.9 times of that of the wild type. The half-lives of the S361R/S444E and G415P/S361R/S444E at 60° C. are respectively 14.9 min and 90.8 min which are respectively 3.2 and 19.7 times of that of the wild type, indicating that the thermal stability of the MTSase mutant consistent with the present disclosure is significantly improved than that of the wild type.

4 Claims, 5 Drawing Sheets

Specification includes a Sequence Listing.

SEQUENCE LISTING

<160> NUMBER OF SEQ ID NOS: 32

<210> SEQ ID NO 1
<211> LENGTH: 757
<212> TYPE: PRT
<213> ORGANISM: Artificial Sequence

```
<220> FEATURE:
<223> OTHER INFORMATION: Protein translated from synthetic DNA

<400> SEQUENCE: 1

Met Pro Ala Ser Thr Tyr Arg Leu Gln Ile Ser Ala Glu Phe Thr Leu
1               5                   10                  15

Phe Asp Ala Ala Arg Ile Val Pro Tyr Leu His Arg Leu Gly Ala Asp
            20                  25                  30

Trp Leu Tyr Leu Ser Pro Leu Leu Glu Ser Glu Ser Gly Ser Ser His
        35                  40                  45

Gly Tyr Asp Val Val Asp His Ser Arg Val Asp Ala Ala Arg Gly Gly
    50                  55                  60

Pro Glu Gly Leu Ala Glu Leu Ser Arg Ala Ala His Glu Arg Gly Met
65                  70                  75                  80

Gly Val Val Val Asp Ile Val Pro Asn His Val Gly Val Ala Thr Pro
                85                  90                  95

Lys Ala Asn Arg Trp Trp Trp Asp Val Leu Ala Arg Gly Gln Arg Ser
            100                 105                 110

Glu Tyr Ala Asp Tyr Phe Asp Ile Asp Trp Glu Phe Gly Gly Gly Arg
        115                 120                 125

Leu Arg Leu Pro Val Leu Gly Asp Gly Pro Asp Glu Leu Asp Ala Leu
    130                 135                 140

Arg Val Asp Gly Asp Glu Leu Val Tyr Tyr Glu His Arg Phe Pro Ile
145                 150                 155                 160

Ala Glu Gly Thr Gly Gly Thr Pro Arg Glu Val His Asp Arg Gln
                165                 170                 175

His Tyr Glu Leu Met Ser Trp Arg Arg Ala Asp His Asp Leu Asn Tyr
            180                 185                 190

Arg Arg Phe Phe Ala Val Asn Thr Leu Ala Ala Val Arg Val Glu Asp
        195                 200                 205

Pro Arg Val Phe Asp Asp Thr His Arg Glu Ile Gly Arg Trp Ile Ala
    210                 215                 220

Glu Gly Leu Val Asp Gly Leu Arg Val Asp His Pro Asp Gly Leu Arg
225                 230                 235                 240

Ala Pro Gly Asp Tyr Leu Arg Arg Leu Ala Glu Leu Ala Gln Gly Arg
                245                 250                 255

Pro Ile Trp Val Glu Lys Ile Ile Glu Gly Asp Glu Arg Met Pro Pro
            260                 265                 270

Gln Trp Pro Ile Ala Gly Thr Thr Gly Tyr Asp Ala Leu Ala Gly Ile
        275                 280                 285

Asp Arg Val Leu Val Asp Pro Ala Gly Glu His Pro Leu Thr Gln Ile
    290                 295                 300

Val Asp Glu Ala Ala Gly Ser Pro Arg Arg Trp Ala Glu Leu Val Pro
305                 310                 315                 320

Glu Arg Lys Arg Ala Val Ala Arg Gly Ile Leu Asn Ser Glu Ile Arg
                325                 330                 335

Arg Val Ala Arg Glu Leu Gly Glu Val Ala Gly Asp Val Glu Asp Ala
            340                 345                 350

Leu Val Glu Ile Ala Ala Leu Ser Val Tyr Arg Ser Tyr Leu Pro
        355                 360                 365

Phe Gly Arg Glu His Leu Asp Glu Ala Val Ala Ala Gln Ala Ala
    370                 375                 380

Ala Pro Gln Leu Glu Ala Asp Leu Ala Ala Val Gly Ala Ala Leu Ala
385                 390                 395                 400
```

Asp Pro Gly Asn Pro Ala Ala Leu Arg Phe Gln Gln Thr Ser Gly Met
            405                 410                 415

Ile Met Ala Lys Gly Val Glu Asp Asn Ala Phe Tyr Arg Tyr Pro Arg
            420                 425                 430

Leu Thr Ser Leu Thr Glu Val Gly Gly Asp Pro Ser Leu Phe Ala Ile
            435                 440                 445

Asp Ala Ala Ala Phe His Ala Ala Gln Arg Asp Arg Ala Ala Arg Leu
        450                 455                 460

Pro Glu Ser Met Thr Thr Leu Thr Thr His Asp Thr Lys Arg Ser Glu
465                 470                 475                 480

Asp Thr Arg Ala Arg Ile Thr Ala Leu Ala Glu Ala Pro Glu Arg Trp
                485                 490                 495

Arg Arg Phe Leu Thr Glu Val Gly Gly Leu Ile Gly Thr Gly Asp Arg
            500                 505                 510

Val Leu Glu Asn Leu Ile Trp Gln Ala Ile Val Gly Ala Trp Pro Ala
            515                 520                 525

Ser Arg Glu Arg Leu Glu Ala Tyr Ala Leu Lys Ala Ala Arg Glu Ala
            530                 535                 540

Gly Glu Ser Thr Asp Trp Ile Asp Gly Asp Pro Ala Phe Glu Glu Arg
545                 550                 555                 560

Leu Thr Arg Leu Val Thr Val Ala Val Glu Glu Pro Leu Val His Glu
                565                 570                 575

Leu Leu Glu Arg Leu Val Asp Glu Leu Thr Ala Ala Gly Tyr Ser Asn
            580                 585                 590

Gly Leu Ala Ala Lys Leu Leu Gln Leu Leu Ala Pro Gly Thr Pro Asp
            595                 600                 605

Val Tyr Gln Gly Thr Glu Arg Trp Asp Arg Ser Leu Val Asp Pro Asp
            610                 615                 620

Asn Arg Arg Pro Val Asp Phe Ala Ala Ala Ser Glu Leu Leu Asp Arg
625                 630                 635                 640

Leu Asp Gly Gly Trp Arg Pro Pro Val Asp Glu Thr Gly Ala Val Lys
                645                 650                 655

Thr Leu Val Val Ser Arg Ala Leu Arg Leu Arg Arg Asp Arg Pro Glu
            660                 665                 670

Leu Phe Thr Ala Tyr His Pro Val Thr Ala Arg Gly Ala Gln Ala Glu
            675                 680                 685

His Leu Ile Gly Phe Asp Arg Gly Gly Ala Ile Ala Leu Ala Thr Arg
            690                 695                 700

Leu Pro Leu Gly Leu Ala Ala Gly Gly Trp Gly Asp Thr Val Val
705                 710                 715                 720

Asp Val Gly Glu Arg Ser Leu Arg Asp Glu Leu Thr Gly Arg Glu Ala
                725                 730                 735

Arg Gly Ala Ala Arg Val Ala Glu Leu Phe Ala Asp Tyr Pro Val Ala
            740                 745                 750

Leu Leu Val Glu Thr
        755

<210> SEQ ID NO 2
<211> LENGTH: 757
<212> TYPE: PRT
<213> ORGANISM: Artificial Sequence
<220> FEATURE:
<223> OTHER INFORMATION: Protein translated from synthetic DNA

<400> SEQUENCE: 2

```
Met Pro Ala Ser Thr Tyr Arg Leu Gln Ile Ser Ala Glu Phe Thr Leu
1               5                   10                  15

Phe Asp Ala Ala Arg Ile Val Pro Tyr Leu His Arg Leu Gly Ala Asp
                20                  25                  30

Trp Leu Tyr Leu Ser Pro Leu Leu Glu Ser Glu Ser Gly Ser Ser His
                35                  40                  45

Gly Tyr Asp Val Val Asp His Ser Arg Val Asp Ala Ala Arg Gly Gly
        50                  55                  60

Pro Glu Gly Leu Ala Glu Leu Ser Arg Ala Ala His Glu Arg Gly Met
65                  70                  75                  80

Gly Val Val Val Asp Ile Val Pro Asn His Val Gly Val Ala Thr Pro
                85                  90                  95

Lys Ala Asn Arg Trp Trp Trp Asp Val Leu Ala Arg Gly Gln Arg Ser
                100                 105                 110

Glu Tyr Ala Asp Tyr Phe Asp Ile Asp Trp Glu Phe Gly Gly Gly Arg
                115                 120                 125

Leu Arg Leu Pro Val Leu Gly Asp Gly Pro Asp Glu Leu Asp Ala Leu
        130                 135                 140

Arg Val Asp Gly Asp Glu Leu Val Tyr Tyr Glu His Arg Phe Pro Ile
145                 150                 155                 160

Ala Glu Gly Thr Gly Gly Gly Thr Pro Arg Glu Val His Asp Arg Gln
                165                 170                 175

His Tyr Glu Leu Met Ser Trp Arg Arg Ala Asp His Asp Leu Asn Tyr
                180                 185                 190

Arg Arg Phe Phe Ala Val Asn Thr Leu Ala Ala Val Arg Val Glu Asp
        195                 200                 205

Pro Arg Val Phe Asp Asp Thr His Arg Glu Ile Gly Arg Trp Ile Ala
        210                 215                 220

Glu Gly Leu Val Asp Gly Leu Arg Val Asp His Pro Asp Gly Leu Arg
225                 230                 235                 240

Ala Pro Gly Asp Tyr Leu Arg Arg Leu Ala Glu Leu Ala Gln Gly Arg
                245                 250                 255

Pro Ile Trp Val Glu Lys Ile Ile Glu Gly Asp Glu Arg Met Pro Pro
                260                 265                 270

Gln Trp Pro Ile Ala Gly Thr Thr Gly Tyr Asp Ala Leu Ala Gly Ile
        275                 280                 285

Asp Arg Val Leu Val Asp Pro Ala Gly Glu His Pro Leu Thr Gln Ile
        290                 295                 300

Val Asp Glu Ala Ala Gly Ser Pro Arg Arg Trp Ala Glu Leu Val Pro
305                 310                 315                 320

Glu Arg Lys Arg Ala Val Ala Arg Gly Ile Leu Asn Ser Glu Ile Arg
                325                 330                 335

Arg Val Ala Arg Glu Leu Gly Glu Val Ala Gly Asp Val Glu Asp Ala
                340                 345                 350

Leu Val Glu Ile Ala Ala Ala Leu Arg Val Tyr Arg Ser Tyr Leu Pro
                355                 360                 365

Phe Gly Arg Glu His Leu Asp Glu Ala Val Ala Ala Gln Ala Ala
        370                 375                 380

Ala Pro Gln Leu Glu Ala Asp Leu Ala Ala Val Gly Ala Ala Leu Ala
385                 390                 395                 400

Asp Pro Gly Asn Pro Ala Ala Leu Arg Phe Gln Gln Thr Ser Gly Met
                405                 410                 415
```

Ile Met Ala Lys Gly Val Glu Asp Asn Ala Phe Tyr Arg Tyr Pro Arg
            420                 425                 430

Leu Thr Ser Leu Thr Glu Val Gly Gly Asp Pro Ser Leu Phe Ala Ile
        435                 440                 445

Asp Ala Ala Ala Phe His Ala Ala Gln Arg Asp Arg Ala Ala Arg Leu
    450                 455                 460

Pro Glu Ser Met Thr Thr Leu Thr Thr His Asp Thr Lys Arg Ser Glu
465                 470                 475                 480

Asp Thr Arg Ala Arg Ile Thr Ala Leu Ala Glu Ala Pro Glu Arg Trp
                485                 490                 495

Arg Arg Phe Leu Thr Glu Val Gly Gly Leu Ile Gly Thr Gly Asp Arg
            500                 505                 510

Val Leu Glu Asn Leu Ile Trp Gln Ala Ile Val Gly Ala Trp Pro Ala
        515                 520                 525

Ser Arg Glu Arg Leu Glu Ala Tyr Ala Leu Lys Ala Ala Arg Glu Ala
    530                 535                 540

Gly Glu Ser Thr Asp Trp Ile Asp Gly Asp Pro Ala Phe Glu Glu Arg
545                 550                 555                 560

Leu Thr Arg Leu Val Thr Val Ala Val Glu Glu Pro Leu Val His Glu
                565                 570                 575

Leu Leu Glu Arg Leu Val Asp Glu Leu Thr Ala Ala Gly Tyr Ser Asn
            580                 585                 590

Gly Leu Ala Ala Lys Leu Leu Gln Leu Leu Ala Pro Gly Thr Pro Asp
        595                 600                 605

Val Tyr Gln Gly Thr Glu Arg Trp Asp Arg Ser Leu Val Asp Pro Asp
    610                 615                 620

Asn Arg Arg Pro Val Asp Phe Ala Ala Ala Ser Glu Leu Leu Asp Arg
625                 630                 635                 640

Leu Asp Gly Gly Trp Arg Pro Pro Val Asp Glu Thr Gly Ala Val Lys
                645                 650                 655

Thr Leu Val Val Ser Arg Ala Leu Arg Leu Arg Arg Asp Arg Pro Glu
            660                 665                 670

Leu Phe Thr Ala Tyr His Pro Val Thr Ala Arg Gly Ala Gln Ala Glu
        675                 680                 685

His Leu Ile Gly Phe Asp Arg Gly Gly Ala Ile Ala Leu Ala Thr Arg
    690                 695                 700

Leu Pro Leu Gly Leu Ala Ala Gly Gly Trp Gly Asp Thr Val Val
705                 710                 715                 720

Asp Val Gly Glu Arg Ser Leu Arg Asp Glu Leu Thr Gly Arg Glu Ala
                725                 730                 735

Arg Gly Ala Ala Arg Val Ala Glu Leu Phe Ala Asp Tyr Pro Val Ala
            740                 745                 750

Leu Leu Val Glu Thr
        755

<210> SEQ ID NO 3
<211> LENGTH: 757
<212> TYPE: PRT
<213> ORGANISM: Artificial Sequence
<220> FEATURE:
<223> OTHER INFORMATION: Protein translated from synthetic DNA

<400> SEQUENCE: 3

Met Pro Ala Ser Thr Tyr Arg Leu Gln Ile Ser Ala Glu Phe Thr Leu
1               5                   10                  15

-continued

```
Phe Asp Ala Ala Arg Ile Val Pro Tyr Leu His Arg Leu Gly Ala Asp
             20                  25                  30

Trp Leu Tyr Leu Ser Pro Leu Leu Glu Ser Glu Ser Gly Ser Ser His
         35                  40                  45

Gly Tyr Asp Val Val Asp His Ser Arg Val Asp Ala Ala Arg Gly Gly
     50                  55                  60

Pro Glu Gly Leu Ala Glu Leu Ser Arg Ala Ala His Glu Arg Gly Met
65                  70                  75                  80

Gly Val Val Val Asp Ile Val Pro Asn His Val Gly Val Ala Thr Pro
                 85                  90                  95

Lys Ala Asn Arg Trp Trp Trp Asp Val Leu Ala Arg Gly Gln Arg Ser
             100                 105                 110

Glu Tyr Ala Asp Tyr Phe Asp Ile Asp Trp Glu Phe Gly Gly Gly Arg
         115                 120                 125

Leu Arg Leu Pro Val Leu Gly Asp Gly Pro Asp Glu Leu Asp Ala Leu
     130                 135                 140

Arg Val Asp Gly Asp Glu Leu Val Tyr Tyr Glu His Arg Phe Pro Ile
145                 150                 155                 160

Ala Glu Gly Thr Gly Gly Gly Thr Pro Arg Glu Val His Asp Arg Gln
                 165                 170                 175

His Tyr Glu Leu Met Ser Trp Arg Arg Ala Asp His Asp Leu Asn Tyr
         180                 185                 190

Arg Arg Phe Phe Ala Val Asn Thr Leu Ala Ala Val Arg Val Glu Asp
     195                 200                 205

Pro Arg Val Phe Asp Asp Thr His Arg Glu Ile Gly Arg Trp Ile Ala
210                 215                 220

Glu Gly Leu Val Asp Gly Leu Arg Val Asp His Pro Asp Gly Leu Arg
225                 230                 235                 240

Ala Pro Gly Asp Tyr Leu Arg Arg Leu Ala Glu Leu Ala Gln Gly Arg
                 245                 250                 255

Pro Ile Trp Val Glu Lys Ile Ile Glu Gly Asp Glu Arg Met Pro Pro
         260                 265                 270

Gln Trp Pro Ile Ala Gly Thr Thr Gly Tyr Asp Ala Leu Ala Gly Ile
     275                 280                 285

Asp Arg Val Leu Val Asp Pro Ala Gly Glu His Pro Leu Thr Gln Ile
290                 295                 300

Val Asp Glu Ala Ala Gly Ser Pro Arg Arg Trp Ala Glu Leu Val Pro
305                 310                 315                 320

Glu Arg Lys Arg Ala Val Ala Arg Gly Ile Leu Asn Ser Glu Ile Arg
                 325                 330                 335

Arg Val Ala Arg Glu Leu Gly Glu Val Ala Gly Asp Val Glu Asp Ala
         340                 345                 350

Leu Val Glu Ile Ala Ala Ala Leu Ser Val Tyr Arg Ser Tyr Leu Pro
     355                 360                 365

Phe Gly Arg Glu His Leu Asp Glu Ala Val Ala Ala Gln Ala Ala
     370                 375                 380

Ala Pro Gln Leu Glu Ala Asp Leu Ala Ala Val Gly Ala Ala Leu Ala
385                 390                 395                 400

Asp Pro Gly Asn Pro Ala Ala Leu Arg Phe Gln Gln Thr Ser Gly Met
                 405                 410                 415

Ile Met Ala Lys Gly Val Glu Asp Asn Ala Phe Tyr Arg Tyr Pro Arg
         420                 425                 430

Leu Thr Ser Leu Thr Glu Val Gly Gly Asp Pro Glu Leu Phe Ala Ile
```

```
                435                 440                 445
Asp Ala Ala Phe His Ala Ala Gln Arg Asp Arg Ala Ala Arg Leu
    450                 455                 460

Pro Glu Ser Met Thr Thr Leu Thr Thr His Asp Thr Lys Arg Ser Glu
465                 470                 475                 480

Asp Thr Arg Ala Arg Ile Thr Ala Leu Ala Glu Ala Pro Glu Arg Trp
                485                 490                 495

Arg Arg Phe Leu Thr Glu Val Gly Gly Leu Ile Gly Thr Gly Asp Arg
            500                 505                 510

Val Leu Glu Asn Leu Ile Trp Gln Ala Ile Val Gly Ala Trp Pro Ala
        515                 520                 525

Ser Arg Glu Arg Leu Glu Ala Tyr Ala Leu Lys Ala Ala Arg Glu Ala
    530                 535                 540

Gly Glu Ser Thr Asp Trp Ile Asp Gly Asp Pro Ala Phe Glu Glu Arg
545                 550                 555                 560

Leu Thr Arg Leu Val Thr Val Ala Val Glu Glu Pro Leu Val His Glu
                565                 570                 575

Leu Leu Glu Arg Leu Val Asp Glu Leu Thr Ala Ala Gly Tyr Ser Asn
            580                 585                 590

Gly Leu Ala Ala Lys Leu Leu Gln Leu Leu Ala Pro Gly Thr Pro Asp
        595                 600                 605

Val Tyr Gln Gly Thr Glu Arg Trp Asp Arg Ser Leu Val Asp Pro Asp
    610                 615                 620

Asn Arg Arg Pro Val Asp Phe Ala Ala Ala Ser Glu Leu Leu Asp Arg
625                 630                 635                 640

Leu Asp Gly Gly Trp Arg Pro Pro Val Asp Glu Thr Gly Ala Val Lys
                645                 650                 655

Thr Leu Val Val Ser Arg Ala Leu Arg Leu Arg Arg Asp Arg Pro Glu
            660                 665                 670

Leu Phe Thr Ala Tyr His Pro Val Thr Ala Arg Gly Ala Gln Ala Glu
        675                 680                 685

His Leu Ile Gly Phe Asp Arg Gly Gly Ala Ile Ala Leu Ala Thr Arg
    690                 695                 700

Leu Pro Leu Gly Leu Ala Ala Ala Gly Gly Trp Gly Asp Thr Val Val
705                 710                 715                 720

Asp Val Gly Glu Arg Ser Leu Arg Asp Glu Leu Thr Gly Arg Glu Ala
                725                 730                 735

Arg Gly Ala Ala Arg Val Ala Glu Leu Phe Ala Asp Tyr Pro Val Ala
            740                 745                 750

Leu Leu Val Glu Thr
            755

<210> SEQ ID NO 4
<211> LENGTH: 757
<212> TYPE: PRT
<213> ORGANISM: Artificial Sequence
<220> FEATURE:
<223> OTHER INFORMATION: Protein translated from synthetic DNA

<400> SEQUENCE: 4

Met Pro Ala Ser Thr Tyr Arg Leu Gln Ile Ser Ala Glu Phe Thr Leu
1               5                   10                  15

Phe Asp Ala Ala Arg Ile Val Pro Tyr Leu His Arg Leu Gly Ala Asp
            20                  25                  30

Trp Leu Tyr Leu Ser Pro Leu Leu Glu Ser Glu Ser Gly Ser Ser His
```

```
            35                  40                  45
Gly Tyr Asp Val Val Asp His Ser Arg Val Asp Ala Ala Arg Gly Gly
 50                  55                  60

Pro Glu Gly Leu Ala Glu Leu Ser Arg Ala Ala His Glu Arg Gly Met
 65                  70                  75                  80

Gly Val Val Val Asp Ile Val Pro Asn His Val Gly Val Ala Thr Pro
                 85                  90                  95

Lys Ala Asn Arg Trp Trp Asp Val Leu Ala Arg Gly Gln Arg Ser
            100                 105                 110

Glu Tyr Ala Asp Tyr Phe Asp Ile Asp Trp Glu Phe Gly Gly Gly Arg
            115                 120                 125

Leu Arg Leu Pro Val Leu Gly Asp Gly Pro Asp Glu Leu Asp Ala Leu
        130                 135                 140

Arg Val Asp Gly Asp Glu Leu Val Tyr Tyr His Arg Phe Pro Ile
145                 150                 155                 160

Ala Glu Gly Thr Gly Gly Gly Thr Pro Arg Glu Val His Asp Arg Gln
                165                 170                 175

His Tyr Glu Leu Met Ser Trp Arg Arg Ala Asp His Asp Leu Asn Tyr
            180                 185                 190

Arg Arg Phe Phe Ala Val Asn Thr Leu Ala Ala Val Arg Val Glu Asp
        195                 200                 205

Pro Arg Val Phe Asp Asp Thr His Arg Glu Ile Gly Arg Trp Ile Ala
210                 215                 220

Glu Gly Leu Val Asp Gly Leu Arg Val Asp His Pro Asp Gly Leu Arg
225                 230                 235                 240

Ala Pro Gly Asp Tyr Leu Arg Arg Leu Ala Glu Leu Ala Gln Gly Arg
                245                 250                 255

Pro Ile Trp Val Glu Lys Ile Ile Glu Gly Asp Glu Arg Met Pro Pro
            260                 265                 270

Gln Trp Pro Ile Ala Gly Thr Thr Gly Tyr Asp Ala Leu Ala Gly Ile
        275                 280                 285

Asp Arg Val Leu Val Asp Pro Ala Gly Glu His Pro Leu Thr Gln Ile
290                 295                 300

Val Asp Glu Ala Ala Gly Ser Pro Arg Arg Trp Ala Glu Leu Val Pro
305                 310                 315                 320

Glu Arg Lys Arg Ala Val Ala Arg Gly Ile Leu Asn Ser Glu Ile Arg
                325                 330                 335

Arg Val Ala Arg Glu Leu Gly Glu Val Ala Gly Asp Val Glu Asp Ala
            340                 345                 350

Leu Val Glu Ile Ala Ala Ala Leu Arg Val Tyr Arg Ser Tyr Leu Pro
        355                 360                 365

Phe Gly Arg Glu His Leu Asp Glu Ala Val Ala Ala Gln Ala Ala
    370                 375                 380

Ala Pro Gln Leu Glu Ala Asp Leu Ala Ala Val Gly Ala Ala Leu Ala
385                 390                 395                 400

Asp Pro Gly Asn Pro Ala Ala Leu Arg Phe Gln Gln Thr Ser Gly Met
                405                 410                 415

Ile Met Ala Lys Gly Val Glu Asp Asn Ala Phe Tyr Tyr Pro Arg
            420                 425                 430

Leu Thr Ser Leu Thr Glu Val Gly Gly Asp Pro Glu Leu Phe Ala Ile
        435                 440                 445

Asp Ala Ala Phe His Ala Gln Arg Asp Arg Ala Ala Arg Leu
450                 455                 460
```

```
Pro Glu Ser Met Thr Thr Leu Thr Thr His Asp Thr Lys Arg Ser Glu
465                 470                 475                 480

Asp Thr Arg Ala Arg Ile Thr Ala Leu Ala Glu Ala Pro Glu Arg Trp
            485                 490                 495

Arg Arg Phe Leu Thr Glu Val Gly Gly Leu Ile Gly Thr Gly Asp Arg
                500                 505                 510

Val Leu Glu Asn Leu Ile Trp Gln Ala Ile Val Gly Ala Trp Pro Ala
            515                 520                 525

Ser Arg Glu Arg Leu Glu Ala Tyr Ala Leu Lys Ala Ala Arg Glu Ala
530                 535                 540

Gly Glu Ser Thr Asp Trp Ile Asp Gly Asp Pro Ala Phe Glu Glu Arg
545                 550                 555                 560

Leu Thr Arg Leu Val Thr Val Ala Val Glu Glu Pro Leu Val His Glu
                565                 570                 575

Leu Leu Glu Arg Leu Val Asp Glu Leu Thr Ala Ala Gly Tyr Ser Asn
                580                 585                 590

Gly Leu Ala Ala Lys Leu Leu Gln Leu Leu Ala Pro Gly Thr Pro Asp
            595                 600                 605

Val Tyr Gln Gly Thr Glu Arg Trp Asp Arg Ser Leu Val Asp Pro Asp
            610                 615                 620

Asn Arg Arg Pro Val Asp Phe Ala Ala Ala Ser Glu Leu Leu Asp Arg
625                 630                 635                 640

Leu Asp Gly Gly Trp Arg Pro Val Asp Glu Thr Gly Ala Val Lys
                645                 650                 655

Thr Leu Val Val Ser Arg Ala Leu Arg Leu Arg Arg Asp Arg Pro Glu
                660                 665                 670

Leu Phe Thr Ala Tyr His Pro Val Thr Ala Arg Gly Ala Gln Ala Glu
            675                 680                 685

His Leu Ile Gly Phe Asp Arg Gly Gly Ala Ile Ala Leu Ala Thr Arg
690                 695                 700

Leu Pro Leu Gly Leu Ala Ala Gly Gly Trp Gly Asp Thr Val Val
705                 710                 715                 720

Asp Val Gly Glu Arg Ser Leu Arg Asp Glu Leu Thr Gly Arg Glu Ala
                725                 730                 735

Arg Gly Ala Ala Arg Val Ala Glu Leu Phe Ala Asp Tyr Pro Val Ala
            740                 745                 750

Leu Leu Val Glu Thr
            755

<210> SEQ ID NO 5
<211> LENGTH: 757
<212> TYPE: PRT
<213> ORGANISM: Artificial Sequence
<220> FEATURE:
<223> OTHER INFORMATION: Protein translated from synthetic DNA

<400> SEQUENCE: 5

Met Pro Ala Ser Thr Tyr Arg Leu Gln Ile Ser Ala Glu Phe Thr Leu
1               5                   10                  15

Phe Asp Ala Ala Arg Ile Val Pro Tyr Leu His Arg Leu Gly Ala Asp
            20                  25                  30

Trp Leu Tyr Leu Ser Pro Leu Leu Glu Ser Glu Ser Gly Ser Ser His
            35                  40                  45

Gly Tyr Asp Val Val Asp His Ser Arg Val Asp Ala Ala Arg Gly Gly
        50                  55                  60
```

```
Pro Glu Gly Leu Ala Glu Leu Ser Arg Ala Ala His Glu Arg Gly Met
65                  70                  75                  80

Gly Val Val Val Asp Ile Val Pro Asn His Val Gly Val Ala Thr Pro
                85                  90                  95

Lys Ala Asn Arg Trp Trp Asp Val Leu Ala Arg Gly Gln Arg Ser
            100                 105                 110

Glu Tyr Ala Asp Tyr Phe Asp Ile Asp Trp Glu Phe Gly Gly Gly Arg
        115                 120                 125

Leu Arg Leu Pro Val Leu Gly Asp Gly Pro Asp Glu Leu Asp Ala Leu
        130                 135                 140

Arg Val Asp Gly Asp Glu Leu Val Tyr Tyr Glu His Arg Phe Pro Ile
145                 150                 155                 160

Ala Glu Gly Thr Gly Gly Gly Thr Pro Arg Glu Val His Asp Arg Gln
                165                 170                 175

His Tyr Glu Leu Met Ser Trp Arg Arg Ala Asp His Asp Leu Asn Tyr
                180                 185                 190

Arg Arg Phe Phe Ala Val Asn Thr Leu Ala Ala Val Arg Val Glu Asp
        195                 200                 205

Pro Arg Val Phe Asp Asp Thr His Arg Glu Ile Gly Arg Trp Ile Ala
        210                 215                 220

Glu Gly Leu Val Asp Gly Leu Arg Val Asp His Pro Asp Gly Leu Arg
225                 230                 235                 240

Ala Pro Gly Asp Tyr Leu Arg Arg Leu Ala Glu Leu Ala Gln Gly Arg
                245                 250                 255

Pro Ile Trp Val Glu Lys Ile Ile Glu Gly Asp Glu Arg Met Pro Pro
                260                 265                 270

Gln Trp Pro Ile Ala Gly Thr Thr Gly Tyr Asp Ala Leu Ala Gly Ile
        275                 280                 285

Asp Arg Val Leu Val Asp Pro Ala Gly Glu His Pro Leu Thr Gln Ile
        290                 295                 300

Val Asp Glu Ala Ala Gly Ser Pro Arg Arg Trp Ala Glu Leu Val Pro
305                 310                 315                 320

Glu Arg Lys Arg Ala Val Ala Arg Gly Ile Leu Asn Ser Glu Ile Arg
                325                 330                 335

Arg Val Ala Arg Glu Leu Gly Glu Val Ala Gly Asp Val Glu Asp Ala
            340                 345                 350

Leu Val Glu Ile Ala Ala Ala Leu Lys Val Tyr Arg Ser Tyr Leu Pro
        355                 360                 365

Phe Gly Arg Glu His Leu Asp Glu Ala Val Ala Ala Gln Ala Ala
    370                 375                 380

Ala Pro Gln Leu Glu Ala Asp Leu Ala Ala Val Gly Ala Ala Leu Ala
385                 390                 395                 400

Asp Pro Gly Asn Pro Ala Ala Leu Arg Phe Gln Gln Thr Ser Gly Met
                405                 410                 415

Ile Met Ala Lys Gly Val Glu Asp Asn Ala Phe Tyr Arg Tyr Pro Arg
            420                 425                 430

Leu Thr Ser Leu Thr Glu Val Gly Gly Asp Pro Glu Leu Phe Ala Ile
                435                 440                 445

Asp Ala Ala Ala Phe His Ala Ala Gln Arg Asp Arg Ala Ala Arg Leu
    450                 455                 460

Pro Glu Ser Met Thr Thr Leu Thr Thr His Asp Thr Lys Arg Ser Glu
465                 470                 475                 480
```

```
Asp Thr Arg Ala Arg Ile Thr Ala Leu Ala Glu Ala Pro Glu Arg Trp
                485                 490                 495

Arg Arg Phe Leu Thr Glu Val Gly Gly Leu Ile Gly Thr Gly Asp Arg
            500                 505                 510

Val Leu Glu Asn Leu Ile Trp Gln Ala Ile Val Gly Ala Trp Pro Ala
        515                 520                 525

Ser Arg Glu Arg Leu Glu Ala Tyr Ala Leu Lys Ala Ala Arg Glu Ala
    530                 535                 540

Gly Glu Ser Thr Asp Trp Ile Asp Gly Asp Pro Ala Phe Glu Glu Arg
545                 550                 555                 560

Leu Thr Arg Leu Val Thr Val Ala Val Glu Glu Pro Leu Val His Glu
                565                 570                 575

Leu Leu Glu Arg Leu Val Asp Glu Leu Thr Ala Ala Gly Tyr Ser Asn
            580                 585                 590

Gly Leu Ala Ala Lys Leu Leu Gln Leu Leu Ala Pro Gly Thr Pro Asp
        595                 600                 605

Val Tyr Gln Gly Thr Glu Arg Trp Asp Arg Ser Leu Val Asp Pro Asp
    610                 615                 620

Asn Arg Arg Pro Val Asp Phe Ala Ala Ala Ser Glu Leu Leu Asp Arg
625                 630                 635                 640

Leu Asp Gly Gly Trp Arg Pro Pro Val Asp Glu Thr Gly Ala Val Lys
                645                 650                 655

Thr Leu Val Val Ser Arg Ala Leu Arg Leu Arg Arg Asp Arg Pro Glu
            660                 665                 670

Leu Phe Thr Ala Tyr His Pro Val Thr Ala Arg Gly Ala Gln Ala Glu
        675                 680                 685

His Leu Ile Gly Phe Asp Arg Gly Gly Ala Ile Ala Leu Ala Thr Arg
    690                 695                 700

Leu Pro Leu Gly Leu Ala Ala Ala Gly Trp Gly Asp Thr Val Val
705                 710                 715                 720

Asp Val Gly Glu Arg Ser Leu Arg Asp Glu Leu Thr Gly Arg Glu Ala
                725                 730                 735

Arg Gly Ala Ala Arg Val Ala Glu Leu Phe Ala Asp Tyr Pro Val Ala
            740                 745                 750

Leu Leu Val Glu Thr
        755

<210> SEQ ID NO 6
<211> LENGTH: 757
<212> TYPE: PRT
<213> ORGANISM: Artificial Sequence
<220> FEATURE:
<223> OTHER INFORMATION: Protein translated from synthetic DNA

<400> SEQUENCE: 6

Met Pro Ala Ser Thr Tyr Arg Leu Gln Ile Ser Ala Glu Phe Thr Leu
1               5                   10                  15

Phe Asp Ala Ala Arg Ile Val Pro Tyr Leu His Arg Leu Gly Ala Asp
                20                  25                  30

Trp Leu Tyr Leu Ser Pro Leu Leu Glu Ser Glu Ser Gly Ser Ser His
            35                  40                  45

Gly Tyr Asp Val Val Asp His Ser Arg Val Asp Ala Ala Arg Gly Gly
        50                  55                  60

Pro Glu Gly Leu Ala Glu Leu Ser Arg Ala Ala His Glu Arg Gly Met
65                  70                  75                  80
```

-continued

```
Gly Val Val Val Asp Ile Val Pro Asn His Val Gly Val Ala Thr Pro
                 85                  90                  95
Lys Ala Asn Arg Trp Trp Asp Val Leu Ala Arg Gly Gln Arg Ser
            100                 105                 110
Glu Tyr Ala Asp Tyr Phe Asp Ile Asp Trp Glu Phe Gly Gly Gly Arg
            115                 120                 125
Leu Arg Leu Pro Val Leu Gly Asp Gly Pro Asp Glu Leu Asp Ala Leu
            130                 135                 140
Arg Val Asp Gly Asp Glu Leu Val Tyr Tyr Glu His Arg Phe Pro Ile
145                 150                 155                 160
Ala Glu Gly Thr Gly Gly Gly Thr Pro Arg Glu Val His Asp Arg Gln
                165                 170                 175
His Tyr Glu Leu Met Ser Trp Arg Arg Ala Asp His Asp Leu Asn Tyr
            180                 185                 190
Arg Arg Phe Phe Ala Val Asn Thr Leu Ala Ala Val Arg Val Glu Asp
            195                 200                 205
Pro Arg Val Phe Asp Asp Thr His Arg Glu Ile Gly Arg Trp Ile Ala
            210                 215                 220
Glu Gly Leu Val Asp Gly Leu Arg Val Asp His Pro Asp Gly Leu Arg
225                 230                 235                 240
Ala Pro Gly Asp Tyr Leu Arg Arg Leu Ala Glu Leu Ala Gln Gly Arg
                245                 250                 255
Pro Ile Trp Val Glu Lys Ile Ile Glu Gly Asp Glu Arg Met Pro Pro
            260                 265                 270
Gln Trp Pro Ile Ala Gly Thr Thr Gly Tyr Asp Ala Leu Ala Gly Ile
            275                 280                 285
Asp Arg Val Leu Val Asp Pro Ala Gly Glu His Pro Leu Thr Gln Ile
            290                 295                 300
Val Asp Glu Ala Ala Gly Ser Pro Arg Arg Trp Ala Glu Leu Val Pro
305                 310                 315                 320
Glu Arg Lys Arg Ala Val Ala Arg Gly Ile Leu Asn Ser Glu Ile Arg
                325                 330                 335
Arg Val Ala Arg Glu Leu Gly Glu Val Ala Gly Asp Val Glu Asp Ala
            340                 345                 350
Leu Val Glu Ile Ala Ala Ala Leu Arg Val Tyr Arg Ser Tyr Leu Pro
            355                 360                 365
Phe Gly Arg Glu His Leu Asp Glu Ala Val Ala Ala Gln Ala Ala
            370                 375                 380
Ala Pro Gln Leu Glu Ala Asp Leu Ala Ala Val Gly Ala Ala Leu Ala
385                 390                 395                 400
Asp Pro Gly Asn Pro Ala Ala Leu Arg Phe Gln Gln Thr Ser Pro Met
                405                 410                 415
Ile Met Ala Lys Gly Val Glu Asp Asn Ala Phe Tyr Arg Tyr Pro Arg
            420                 425                 430
Leu Thr Ser Leu Thr Glu Val Gly Gly Asp Pro Glu Leu Phe Ala Ile
            435                 440                 445
Asp Ala Ala Ala Phe His Ala Ala Gln Arg Asp Arg Ala Ala Arg Leu
450                 455                 460
Pro Glu Ser Met Thr Thr Leu Thr Thr His Asp Thr Lys Arg Ser Glu
465                 470                 475                 480
Asp Thr Arg Ala Arg Ile Thr Ala Leu Ala Glu Ala Pro Glu Arg Trp
                485                 490                 495
Arg Arg Phe Leu Thr Glu Val Gly Gly Leu Ile Gly Thr Gly Asp Arg
```

```
                500                 505                 510
        Val Leu Glu Asn Leu Ile Trp Gln Ala Ile Val Gly Ala Trp Pro Ala
            515                 520                 525

Ser Arg Glu Arg Leu Glu Ala Tyr Ala Leu Lys Ala Ala Arg Glu Ala
            530                 535                 540

Gly Glu Ser Thr Asp Trp Ile Asp Gly Asp Pro Ala Phe Glu Glu Arg
        545                 550                 555                 560

Leu Thr Arg Leu Val Thr Val Ala Val Glu Glu Pro Leu Val His Glu
                        565                 570                 575

Leu Leu Glu Arg Leu Val Asp Glu Leu Thr Ala Ala Gly Tyr Ser Asn
                    580                 585                 590

Gly Leu Ala Ala Lys Leu Leu Gln Leu Leu Ala Pro Gly Thr Pro Asp
                    595                 600                 605

Val Tyr Gln Gly Thr Glu Arg Trp Asp Arg Ser Leu Val Asp Pro Asp
                610                 615                 620

Asn Arg Arg Pro Val Asp Phe Ala Ala Ala Ser Glu Leu Leu Asp Arg
        625                 630                 635                 640

Leu Asp Gly Gly Trp Arg Pro Pro Val Asp Glu Thr Gly Ala Val Lys
                        645                 650                 655

Thr Leu Val Val Ser Arg Ala Leu Arg Leu Arg Arg Asp Arg Pro Glu
                    660                 665                 670

Leu Phe Thr Ala Tyr His Pro Val Thr Ala Arg Gly Ala Gln Ala Glu
                    675                 680                 685

His Leu Ile Gly Phe Asp Arg Gly Gly Ala Ile Ala Leu Ala Thr Arg
                690                 695                 700

Leu Pro Leu Gly Leu Ala Ala Ala Gly Gly Trp Gly Asp Thr Val Val
        705                 710                 715                 720

Asp Val Gly Glu Arg Ser Leu Arg Asp Glu Leu Thr Gly Arg Glu Ala
                        725                 730                 735

Arg Gly Ala Ala Arg Val Ala Glu Leu Phe Ala Asp Tyr Pro Val Ala
                    740                 745                 750

Leu Leu Val Glu Thr
                    755

<210> SEQ ID NO 7
<211> LENGTH: 2274
<212> TYPE: DNA
<213> ORGANISM: Artificial Sequence
<220> FEATURE:
<223> OTHER INFORMATION: Synthetic DNA

<400> SEQUENCE: 7
atgccagctt ctacatatcg tttacagatt tcagccgagt tcaccttatt tgatgcagcc    60
cgtattgttc catatctgca tcgtttaggc gccgattggt tatatctgag tcctctgtta   120
gaaagtgaat caggttcttc acatggctat gatgttgtgg atcattcgag ggtggatgca   180
gctcgcggcg gtccggaagg tctggccgaa ctgtcacgcg cagcccatga acgcggtatg   240
ggcgttgttg tggatattgt tcctaatcat gtgggtgttg caacccctaa agctaatcgt   300
tggtggtggg atgttctggc acgcggtcag cgtagtgaat atgccgatta ttttgacatc   360
gattgggaat tggtggcgg tcgcttacgc ttacctgtgt aggcgatgg tccggatgaa   420 ttagatgcac tgcgcgtgga tggcgatgaa ttagtgtatt atgaacatcg ttttcctatt   480
gcggaaggta cgggcggtgg aaccccacgc gaagttcatg atcgtcagca ttatgaatta   540
atgtcttggc gccgtgccga tcatgatttg aattatcgtc gcttcttcgc tgttaataca   600
```

```
ctggccgccg ttcgtgtgga agatcctcgc gttttttgatg atacacatcg cgaaatcggt    660
cgctggattg cggaaggctt agttgatggt cttcgcgtgg atcatccgga tggtctgcgt    720
gctccgggcg attatctgcg tcgtttagcc gaattagctc agggtcgtcc tatttgggtt    780
gaaaaaatca tcgaagggga tgaacgtatg ccacctcagt ggccaattgc gggtacaacc    840
ggctatgatg ccctggcagg catcgatcgt gttctggttg atccagcggg cgaacatcct    900
ctgacacaga ttgtggatga agctgccggc tctccacgtc gctgggcaga actggttcca    960
gaacgtaaac gtgcagttgc ccgtggtatc ttaaatagcg aaattcgtcg cgttgctcgc   1020
gaattaggcg aagttgcggg cgatgtggaa gatgccttag tggaaattgc tgctgctctg   1080
tcagtgtatc gtagctactt accatttggc cgtgaacatc tggatgaagc agttgctgcc   1140
gcacaggcag ctgccccaca gttagaagca gacttggctg ctgtgggcgc cgccctggcc   1200
gatccgggca atccggctgc gttacgcttt cagcagacct caggtatgat catggccaaa   1260
ggtgtggaag ataatgcctt ttatcgctat cctcgcctga cctcactgac ggaagtgggc   1320
ggtgacccct cactgttttgc aatcgatgct gctgcctttc atgcggcaca gcgcgatcgt   1380
gcggcccgtc tgccagaaag tatgacaacc ctgacaaccc atgataccaa acgctcagaa   1440
gatactaggg cccgcatcac cgccttagca gaagctccgg aacgttggcg tcgctttctg   1500
acggaagtgg gcggtctgat tggtactggg gatcgcgttt tagaaaacct catctggcag   1560
gccattgtgg gtgcttggcc agcgagtcgc gaacgcctgg aagcgtacgc cttaaaagcc   1620
gctagagaag caggtgaaag taccgattgg attgatggag atccggcctt tgaagaacgc   1680
ctgacccgcc tggttacggt tgctgtggaa gaaccattag ttcatgaatt attagaacgc   1740
ttagttgatg aactgaccgc cgcaggctat agtaatggct tagccgccaa actgttacag   1800
ttactggcac cgggtacacc agatgtgtat cagggtacgg aacgctggga tcgtagttta   1860
gttgatccag ataatcgtcg tccggttgat tttgcggcgg ccagtgaact gttagatcgc   1920
ttagatggcg gttggcgtcc accagtggat gaaacaggtg cagttaaaac actggttgtg   1980
tctcgcgcac tgcgcttacg tcgcgatcgt ccagaattat tcaccgcata tcatccagtg   2040
acggcacgcg gtgctcaggc tgaacatctt atcggctttg atcgcggcgg tgcaattgcc   2100
ctggcaaccc gtttaccatt aggcttagcc gcagcgggcg gctggggaga taccgttgtt   2160
gatgtgggtg aacgtagtct gcgcgatgaa ctgacgggtc gtgaagcccg cggcgcagcg   2220 cggggttgccg aactgtttgc agattatcca gttgcattac tggttgaaac ctaa         2274
```

<210> SEQ ID NO 8
<211> LENGTH: 34
<212> TYPE: DNA
<213> ORGANISM: Artificial Sequence
<220> FEATURE:
<223> OTHER INFORMATION: Synthetic DNA

<400> SEQUENCE: 8

```
ctgctgctct gcgcgtgtat cgtagctact tacc                                 34
```

<210> SEQ ID NO 9
<211> LENGTH: 34
<212> TYPE: DNA
<213> ORGANISM: Artificial Sequence
<220> FEATURE:
<223> OTHER INFORMATION: Synthetic DNA

<400> SEQUENCE: 9
ggtaagtagc tacgatacac gcgcagagca gcag        34

<210> SEQ ID NO 10
<211> LENGTH: 31
<212> TYPE: DNA
<213> ORGANISM: Artificial Sequence
<220> FEATURE:
<223> OTHER INFORMATION: Synthetic DNA

<400> SEQUENCE: 10
gcggtgaccc tgaactgttt gcaatcgatg c        31

<210> SEQ ID NO 11
<211> LENGTH: 31
<212> TYPE: DNA
<213> ORGANISM: Artificial Sequence
<220> FEATURE:
<223> OTHER INFORMATION: Synthetic DNA

<400> SEQUENCE: 11
gcatcgattg caaacagttc agggtcaccg c        31

<210> SEQ ID NO 12
<211> LENGTH: 32
<212> TYPE: DNA
<213> ORGANISM: Artificial Sequence
<220> FEATURE:
<223> OTHER INFORMATION: Synthetic DNA

<400> SEQUENCE: 12
tgctctgaaa gtgtatcgta gctacttacc at        32

<210> SEQ ID NO 13
<211> LENGTH: 27
<212> TYPE: DNA
<213> ORGANISM: Artificial Sequence
<220> FEATURE:
<223> OTHER INFORMATION: Synthetic DNA

<400> SEQUENCE: 13
acactttcag agcagcagca atttcca        27

<210> SEQ ID NO 14
<211> LENGTH: 30
<212> TYPE: DNA
<213> ORGANISM: Artificial Sequence
<220> FEATURE:
<223> OTHER INFORMATION: Synthetic DNA

<400> SEQUENCE: 14
gctctgcaag tgtatcgtag ctacttacca        30

<210> SEQ ID NO 15
<211> LENGTH: 26
<212> TYPE: DNA
<213> ORGANISM: Artificial Sequence
<220> FEATURE:
<223> OTHER INFORMATION: Synthetic DNA

<400> SEQUENCE: 15
cacttgcaga gcagcagcaa tttcca        26

<210> SEQ ID NO 16
<211> LENGTH: 29
<212> TYPE: DNA
<213> ORGANISM: Artificial Sequence
<220> FEATURE:
<223> OTHER INFORMATION: Synthetic DNA

<400> SEQUENCE: 16
gaccctcaac tgtttgcaat cgatgctgc                29

<210> SEQ ID NO 17
<211> LENGTH: 25
<212> TYPE: DNA
<213> ORGANISM: Artificial Sequence
<220> FEATURE:
<223> OTHER INFORMATION: Synthetic DNA

<400> SEQUENCE: 17
acagttgagg gtcaccgccc acttc                    25

<210> SEQ ID NO 18
<211> LENGTH: 26
<212> TYPE: DNA
<213> ORGANISM: Artificial Sequence
<220> FEATURE:
<223> OTHER INFORMATION: Synthetic DNA

<400> SEQUENCE: 18
cctttactgt ttgcaatcga tgctgc                   26

<210> SEQ ID NO 19
<211> LENGTH: 26
<212> TYPE: DNA
<213> ORGANISM: Artificial Sequence
<220> FEATURE:
<223> OTHER INFORMATION: Synthetic DNA

<400> SEQUENCE: 19
gcaaacagta aagggtcacc gcccac                   26

<210> SEQ ID NO 20
<211> LENGTH: 36
<212> TYPE: DNA
<213> ORGANISM: Artificial Sequence
<220> FEATURE:
<223> OTHER INFORMATION: Synthetic DNA

<400> SEQUENCE: 20
cagcagacct caccgatgat catggccaaa ggtgtg        36

<210> SEQ ID NO 21
<211> LENGTH: 36
<212> TYPE: DNA
<213> ORGANISM: Artificial Sequence
<220> FEATURE:
<223> OTHER INFORMATION: Synthetic DNA

<400> SEQUENCE: 21
cacacctttg gccatgatca tcggtgaggt ctgctg        36

<210> SEQ ID NO 22
<211> LENGTH: 30
<212> TYPE: DNA
<213> ORGANISM: Artificial Sequence
<220> FEATURE:
<223> OTHER INFORMATION: Synthetic DNA

<400> SEQUENCE: 22
ctttcagcag acctcagata tgatcatggc               30

<210> SEQ ID NO 23
<211> LENGTH: 30
<212> TYPE: DNA
<213> ORGANISM: Artificial Sequence
<220> FEATURE:
<223> OTHER INFORMATION: Synthetic DNA

<400> SEQUENCE: 23
gccatgatca tatctgaggt ctgctgaaag                                       30

<210> SEQ ID NO 24
<211> LENGTH: 35
<212> TYPE: DNA
<213> ORGANISM: Artificial Sequence
<220> FEATURE:
<223> OTHER INFORMATION: Synthetic DNA

<400> SEQUENCE: 24
cagcccgtat tgttccatat tttcatcgtt taggc                                 35

<210> SEQ ID NO 25
<211> LENGTH: 35
<212> TYPE: DNA
<213> ORGANISM: Artificial Sequence
<220> FEATURE:
<223> OTHER INFORMATION: Synthetic DNA

<400> SEQUENCE: 25
gcctaaacga tgaaatatg gaacaatacg ggctg                                  35

<210> SEQ ID NO 26
<211> LENGTH: 33
<212> TYPE: DNA
<213> ORGANISM: Artificial Sequence
<220> FEATURE:
<223> OTHER INFORMATION: Synthetic DNA

<400> SEQUENCE: 26
cgctttcagc agtactcagg tatgatcatg gcc                                   33

<210> SEQ ID NO 27
<211> LENGTH: 33
<212> TYPE: DNA
<213> ORGANISM: Artificial Sequence
<220> FEATURE:
<223> OTHER INFORMATION: Synthetic DNA

<400> SEQUENCE: 27
ggccatgatc atacctgagt actgctgaaa gcg                                   33

<210> SEQ ID NO 28
<211> LENGTH: 31
<212> TYPE: DNA
<213> ORGANISM: Artificial Sequence
<220> FEATURE:
<223> OTHER INFORMATION: Synthetic DNA

<400> SEQUENCE: 28
cacctcagtg gccaattgat ggtacaaccg g                                     31

<210> SEQ ID NO 29
<211> LENGTH: 31
<212> TYPE: DNA
<213> ORGANISM: Artificial Sequence
<220> FEATURE:
<223> OTHER INFORMATION: Synthetic DNA

<400> SEQUENCE: 29
ccggttgtac catcaattgg ccactgaggt g        31

<210> SEQ ID NO 30
<211> LENGTH: 757
<212> TYPE: PRT
<213> ORGANISM: Artificial Sequence
<220> FEATURE:
<223> OTHER INFORMATION: Protein translated from synthetic DNA

<400> SEQUENCE: 30

```
Met Pro Ala Ser Thr Tyr Arg Leu Gln Ile Ser Ala Glu Phe Thr Leu
 1               5                  10                  15

Phe Asp Ala Ala Arg Ile Val Pro Tyr Leu His Arg Leu Gly Ala Asp
                20                  25                  30

Trp Leu Tyr Leu Ser Pro Leu Leu Glu Ser Glu Ser Gly Ser Ser His
            35                  40                  45

Gly Tyr Asp Val Val Asp His Ser Arg Val Asp Ala Ala Arg Gly Gly
        50                  55                  60

Pro Glu Gly Leu Ala Glu Leu Ser Arg Ala Ala His Glu Arg Gly Met
65                  70                  75                  80

Gly Val Val Val Asp Ile Val Pro Asn His Val Gly Val Ala Thr Pro
                85                  90                  95

Lys Ala Asn Arg Trp Trp Trp Asp Val Leu Ala Arg Gly Gln Arg Ser
               100                 105                 110

Glu Tyr Ala Asp Tyr Phe Asp Ile Asp Trp Glu Phe Gly Gly Gly Arg
           115                 120                 125

Leu Arg Leu Pro Val Leu Gly Asp Gly Pro Asp Glu Leu Asp Ala Leu
       130                 135                 140

Arg Val Asp Gly Asp Glu Leu Val Tyr Tyr Glu His Arg Phe Pro Ile
145                 150                 155                 160

Ala Glu Gly Thr Gly Gly Gly Thr Pro Arg Glu Val His Asp Arg Gln
               165                 170                 175

His Tyr Glu Leu Met Ser Trp Arg Arg Ala Asp His Asp Leu Asn Tyr
           180                 185                 190

Arg Arg Phe Phe Ala Val Asn Thr Leu Ala Ala Val Arg Val Glu Asp
       195                 200                 205

Pro Arg Val Phe Asp Asp Thr His Arg Glu Ile Gly Arg Trp Ile Ala
   210                 215                 220

Glu Gly Leu Val Asp Gly Leu Arg Val Asp His Pro Asp Gly Leu Arg
225                 230                 235                 240

Ala Pro Gly Asp Tyr Leu Arg Arg Leu Ala Glu Leu Ala Gln Gly Arg
               245                 250                 255

Pro Ile Trp Val Glu Lys Ile Ile Glu Gly Asp Glu Arg Met Pro Pro
           260                 265                 270

Gln Trp Pro Ile Ala Gly Thr Thr Gly Tyr Asp Ala Leu Ala Gly Ile
       275                 280                 285

Asp Arg Val Leu Val Asp Pro Ala Gly Glu His Pro Leu Thr Gln Ile
   290                 295                 300

Val Asp Glu Ala Ala Gly Ser Pro Arg Arg Trp Ala Glu Leu Val Pro
305                 310                 315                 320

Glu Arg Lys Arg Ala Val Ala Arg Gly Ile Leu Asn Ser Glu Ile Arg
               325                 330                 335

Arg Val Ala Arg Glu Leu Gly Glu Val Ala Gly Asp Val Glu Asp Ala
```

```
                340             345             350
Leu Val Glu Ile Ala Ala Ala Leu Ser Val Tyr Arg Ser Tyr Leu Pro
            355             360             365
Phe Gly Arg Glu His Leu Asp Glu Ala Val Ala Ala Gln Ala Ala
370             375             380
Ala Pro Gln Leu Glu Ala Asp Leu Ala Ala Val Gly Ala Ala Leu Ala
385             390             395             400
Asp Pro Gly Asn Pro Ala Ala Leu Arg Phe Gln Gln Thr Ser Pro Met
                405             410             415
Ile Met Ala Lys Gly Val Glu Asp Asn Ala Phe Tyr Arg Tyr Pro Arg
            420             425             430
Leu Thr Ser Leu Thr Glu Val Gly Gly Asp Pro Ser Leu Phe Ala Ile
            435             440             445
Asp Ala Ala Ala Phe His Ala Ala Gln Arg Asp Arg Ala Ala Arg Leu
            450             455             460
Pro Glu Ser Met Thr Thr Leu Thr Thr His Asp Thr Lys Arg Ser Glu
465             470             475             480
Asp Thr Arg Ala Arg Ile Thr Ala Leu Ala Glu Ala Pro Glu Arg Trp
                485             490             495
Arg Arg Phe Leu Thr Glu Val Gly Gly Leu Ile Gly Thr Gly Asp Arg
            500             505             510
Val Leu Glu Asn Leu Ile Trp Gln Ala Ile Val Gly Ala Trp Pro Ala
            515             520             525
Ser Arg Glu Arg Leu Glu Ala Tyr Ala Leu Lys Ala Ala Arg Glu Ala
            530             535             540
Gly Glu Ser Thr Asp Trp Ile Asp Gly Asp Pro Ala Phe Glu Glu Arg
545             550             555             560
Leu Thr Arg Leu Val Thr Val Ala Val Glu Glu Pro Leu Val His Glu
                565             570             575
Leu Leu Glu Arg Leu Val Asp Glu Leu Thr Ala Ala Gly Tyr Ser Asn
            580             585             590
Gly Leu Ala Ala Lys Leu Leu Gln Leu Leu Ala Pro Gly Thr Pro Asp
            595             600             605
Val Tyr Gln Gly Thr Glu Arg Trp Asp Arg Ser Leu Val Asp Pro Asp
            610             615             620
Asn Arg Arg Pro Val Asp Phe Ala Ala Ala Ser Glu Leu Leu Asp Arg
625             630             635             640
Leu Asp Gly Gly Trp Arg Pro Val Asp Glu Thr Gly Ala Val Lys
                645             650             655
Thr Leu Val Val Ser Arg Ala Leu Arg Leu Arg Arg Asp Arg Pro Glu
            660             665             670
Leu Phe Thr Ala Tyr His Pro Val Thr Ala Arg Gly Ala Gln Ala Glu
            675             680             685
His Leu Ile Gly Phe Asp Arg Gly Gly Ala Ile Ala Leu Ala Thr Arg
            690             695             700
Leu Pro Leu Gly Leu Ala Ala Ala Gly Gly Trp Gly Asp Thr Val Val
705             710             715             720
Asp Val Gly Glu Arg Ser Leu Arg Asp Glu Leu Thr Gly Arg Glu Ala
                725             730             735
Arg Gly Ala Ala Arg Val Ala Glu Leu Phe Ala Asp Tyr Pro Val Ala
            740             745             750
Leu Leu Val Glu Thr
            755
```

```
<210> SEQ ID NO 31
<211> LENGTH: 31
<212> TYPE: DNA
<213> ORGANISM: Artificial Sequence
<220> FEATURE:
<223> OTHER INFORMATION: Synthetic DNA

<400> SEQUENCE: 31
gctttcagca gacctcaccg atgatcatgg c                              31

<210> SEQ ID NO 32
<211> LENGTH: 31
<212> TYPE: DNA
<213> ORGANISM: Artificial Sequence
<220> FEATURE:
<223> OTHER INFORMATION: Synthetic DNA

<400> SEQUENCE: 32
gccatgatca tcggtgaggt ctgctgaaag c                              31
```

MALTOOLIGOSYL TREHALOSE SYNTHASE MUTANT WITH IMPROVED THERMAL STABILITY

TECHNICAL FIELD

The present disclosure relates to a maltooligosyl trehalose synthase mutant with improved thermal stability, and belongs to the technical fields of enzyme engineering and protein engineering.

BACKGROUND

Trehalose is a non-reducing sugar formed by the linkage of two glucoses through an α,α-1,1-glycosidic bond. Trehalose was originally isolated by Wiggers from *Claviceps purpurea* of ryegrass, and is widely found in bacteria, fungi, yeast, lower ferns, algae, insects and invertebrates.

In addition to being a structural component and providing energy in creatures, trehalose plays a most important role as a typical stress metabolite, and protects proteins, lipids, sugars, nucleic acids and other components in cells in the creatures from damage under many environmental conditions such as dryness, low temperature and hypertonicity, thereby protecting the cells from damage. Therefore, trehalose has become an important protective agent for biological activity preservation of vaccines, enzymes, living tissues and cells. At the same time, trehalose has high stability to acid and heat, can prevent starch aging and protein denaturation, can inhibit fat rancidity, has a flavor and odor modifying function, and has high glass transition temperature, low hygroscopicity and low sweetness. These properties make trehalose widely used in food processing, pharmaceutical, agricultural, biochemical and cosmetic industries, and become an additive to tens of thousands of products.

Since the 1980s, countries have carried out research on physiology, biochemistry and molecular biology of trehalose. At present, trehalose has become one of the major oligosaccharides recently developed internationally. China's Ministry of Health also officially approved trehalose as a new resource food in 2005.

There are three main methods for producing trehalose, namely an acidification enzyme method, a trehalose synthase single enzyme method, and a maltooligosyl trehalose synthase (MTSase) and maltooligosyl trehalose hydrolase (MTHase) double enzyme method. Among them, the MTSase and MTHase double enzyme method produces trehalose by using liquefied starch as a substrate for carrying out concerted reaction with the MTSase and MTHase enzymes. The trehalose produced by this method has a high conversion rate and few by-products. Moreover, this method can utilize inexpensive starch as a substrate, which undoubtedly greatly reduces the production cost of trehalose. Therefore, the MTSase and MTHase double enzyme method has gradually become one of the most important methods of trehalose production.

The process of preparing trehalose by the MTSase and MTHase double enzyme method is as follows: firstly, starch is sequentially subjected to high temperature liquefaction and pullulanase action to form maltodextrin; then, MTSase is added to act on the α,α-1,4-glycoside at the reducing end of the maltodextrin substrate, and the intramolecular transglycosylation of the α,α-1,1-glycosidic bond is exerted to form an product intermediate maltooligosyl trehalose. The MTHase specifically internally digests the α,α-1,4-glycosidic bond where the maltooligosyl and trehalose in maltooligosyl trehalose are connected, and the maltooligosyl trehalose is decomposed to produce trehalose and new malt oligosaccharide with two glucose units reduced. The new malt oligosaccharide with two glucose units reduced serves as a new substrate for the next round of reactions. By repeating the two enzyme reactions in this way, the malt oligosaccharide can be converted into a product mainly composed of trehalose and containing a small amount of glucose, maltose, and maltotriose.

From this process, maltooligosyl trehalose synthase (MTSase) is the key to the preparation of trehalose by the MTSase and MTHase double enzyme method. Obtainment of MTSase (maltooligosyl trehalose synthase) with more advantages in production is undoubtedly important to produce trehalose.

There are two types of maltooligosyl trehalose synthase, namely a high temperature enzyme applicable at above 60° C. and a medium temperature enzyme applicable at 40-45° C. Among them, the high temperature enzyme is poorly expressed in a host, has lower specific enzyme activity than the medium temperature enzyme, and is not applicable to actual production. The medium temperature enzyme is less thermally stable, so the temperature cannot be too high when the medium temperature enzyme is used for conversion reaction. When the reaction temperature cannot be too high, the reaction process is likely to be contaminated, and at the same time, the enzyme needs to be supplemented during the reaction, and the cost is high. Therefore, there is an urgent need to find a medium temperature enzyme with improved thermal stability to solve the defects of the existing medium temperature enzyme in trehalose production.

SUMMARY

The present disclosure provides a maltooligosyl trehalose synthase mutant (MTSase, EC 5.4.99.15) with improved thermal stability.

The enzyme mutant is obtained by mutating the $415^{th}$ amino acid of maltooligosyl trehalose synthase with the starting amino acid sequence as shown in SEQ ID NO.1;

Or, the enzyme mutant is obtained by mutating the $361^{st}$ and/or the $444^{th}$ amino acids of maltooligosyl trehalose synthase with the starting amino acid sequence as shown in SEQ ID NO.1;

Or, the enzyme mutant is obtained by simultaneously mutating the $361^{st}$, the $444^{th}$ and the $415^{th}$ amino acids of maltooligosyl trehalose synthase with the starting amino acid sequence as shown in SEQ ID NO.1.

In one example of the present disclosure, the enzyme mutant is obtained by mutating the $415^{th}$ glycine of the maltooligosyl trehalose synthase with the starting amino acid sequence as shown in SEQ ID NO.1 into proline, and is named G415P;

Or, the enzyme mutant is obtained by mutating the $361^{st}$ serine of maltooligosyl trehalose synthase with the starting amino acid sequence as shown in SEQ ID NO.1 into arginine, and is named S361R;

Or, the enzyme mutant is obtained by mutating the $444^{th}$ serine of maltooligosyl trehalose synthase with the starting amino acid sequence as shown in SEQ ID NO.1 into glutamic acid, and is named S444E;

Or, the enzyme mutant is obtained by mutating the $361^{st}$ serine and the $444^{th}$ serine of maltooligosyl trehalose synthase with the starting amino acid sequence as shown in SEQ ID NO.1 into arginine and glutamic acid respectively, and is named S361R/S444E;

Or, the enzyme mutant is obtained by mutating the 361st serine and the 444th serine of maltooligosyl trehalose synthase with the starting amino acid sequence as shown in SEQ ID NO.1 into lysine and glutamic acid respectively, and is named S361K/S444E;

Or, the enzyme mutant is obtained by mutating the 361st serine, the 444th serine and the 415th glycine of maltooligosyl trehalose synthase with the starting amino acid sequence as shown in SEQ ID NO.1 into arginine, glutamic acid and proline respectively, and is named G415P/S361R/S444E.

In one example of the present disclosure, the amino acid sequence of the maltooligosyl trehalose synthase mutant is as shown in SEQ ID NO.2, SEQ ID NO.3, SEQ ID NO.4, SEQ ID NO.5, SEQ ID NO.6 or SEQ ID NO.30.

In one example of the present disclosure, the maltooligosyl trehalose synthase is derived from *Arthrobacter ramosus*.

The present disclosure also provides a gene for coding the maltooligosyl trehalose synthase mutant.

The present disclosure also provides a recombinant plasmid carrying the above gene.

In one example of the present disclosure, the recombinant plasmid vector is a pUC plasmid, a pET plasmid or a pGEX plasmid.

The present disclosure also provides a host cell carrying the gene or the recombinant plasmid.

In one example of the present disclosure, the host cell is bacteria or fungi.

In one example of the present disclosure, the host cell is *Escherichia coli*.

The present disclosure also provides a preparation method of the maltooligosyl trehalose synthase mutant, comprising: inoculating a fermentation medium with the host cell, carrying out fermentation, collecting bacteria obtained by fermentation after fermentation, crushing the bacteria, and after crushing, separating the maltooligosyl trehalose synthase mutant from the disrupted cell suspension obtained by crushing.

In one example of the present disclosure, the fermentation medium is an LB medium or a TB medium.

The present disclosure also provides application of the maltooligosyl trehalose synthase mutant or the gene or the recombinant plasmid or the host cell in producing trehalose.

The present disclosure also provides a method for producing trehalose, comprising: adding α-amylase to a starch solution to carry out liquefaction to obtain enzymatic hydrolysate; and adding pullulanase, cyclodextrin glucosyltransferase, 4-α glycosyltransferase and the maltooligosyl trehalose synthase mutant to the enzymatic hydrolysate to carry out a reaction to obtain the trehalose.

In one example of the present disclosure, the addition amount of the maltooligosyl trehalose synthase mutant to the enzymatic hydrolysate is 2-8 U/mL.

In one example of the present disclosure, the method comprises: adding α-amylase to the starch solution to carry out liquefaction until a DE value is 16 to obtain enzymatic hydrolysate; adding pullulanase, cyclodextrin glucosyltransferase, 4-α glycosyltransferase and the maltooligosyl trehalose synthase mutant to the enzymatic hydrolysate to carry out a reaction to obtain the trehalose.

In one example of the present disclosure, the concentration of the starch solution is 150 g/L; the addition amount of the α-amylase in the starch solution is 0.5 U/mL; the addition amount of the pullulanase in the enzymatic hydrolysate is 5 U/g starch; the addition amount of the cyclodextrin glucosyltransferase in the enzymatic hydrolysate is 2 U/mL; the addition amount of the 4-α glycosyltransferase in the enzymatic hydrolysate is 0.5 U/mL; and the addition amount of the maltooligosyl trehalose synthase mutant in the enzymatic hydrolysate is 5 U/mL.

In one example of the present disclosure, liquefaction is carried out at the conditions of pH 5.5 and 90° C. for 8-10 min.

In one example of the present disclosure, reaction is carried out at the conditions of 60° C. and 150 r/min for 36 h.

Beneficial Effects:

(1) The residual enzyme activities of the maltooligosyl trehalose synthase mutants S361R, S444E, S361R/S444E, S361K/S444E, G415P/S361R/S444E and G415P consistent with the present disclosure after treatment at 60° C. for 10 min are 70.3%, 50.1%, 83.5%, 65.9%, 100% and 80.7% respectively, which are respectively 1.6 times, 1.1 times, 1.9 times, 1.5 times, 2.3 times and 1.9 times of that of a wild type, indicating that the thermal stability of the maltooligosyl trehalose synthase mutants S361R, S444E, S361R/S444E, S361K/S444E, G415P/S361R/S444E and G415P consistent with the present disclosure is significantly improved;

(2) The half-life of the maltooligosyl trehalose synthase mutant G415P consistent with the present disclosure is 41 h longer than that of the wild type at 50° C., and is twice that of the wild type, indicating that the thermal stability of the maltooligosyl trehalose synthase mutant G415P consistent with the present disclosure is significantly improved;

(3) The half-lives of the maltooligosyl trehalose synthase mutants S361R/S444E and G415P/S361R/S444E consistent with the present disclosure are respectively 10.3 min and 86.2 min longer than that of the wild type at 60° C., which are 3.2 times and 19.7 times of the wild type, indicating that the thermal stability of the maltooligosyl trehalose synthase mutants S361R/S444E and G415P/S361R/S444E consistent with the present disclosure is significantly improved;

(4) When the maltooligosyl trehalose synthase mutant G415P consistent with the present disclosure is used for producing trehalose, the optimal enzyme amount is 2.0 U/mL, while the optimal enzyme amount of the wild type is 2.5 U/mL, and the conversion rates of the two are 63.6% and 64.0% respectively, indicating that while the stability of the maltooligosyl trehalose synthase mutant G415P consistent with the present disclosure is improved, the enzyme amount is reduced, and the conversion rate is almost not influenced;

(5) The conversion rate of trehalose produced by using the maltooligosyl trehalose synthase mutant G415P/S361R/S444E consistent with the present disclosure at 60° C. is up to 65.3%, which is improved by 20.2% compared with the wild type, further proving that the maltooligosyl trehalose synthase mutant G415P/S361R/S444E consistent with the present disclosure has significantly improved thermal stability, can produce trehalose at higher temperatures and has a higher conversion rate than that of the wild type.

DETAILED DESCRIPTION

Figure 1:
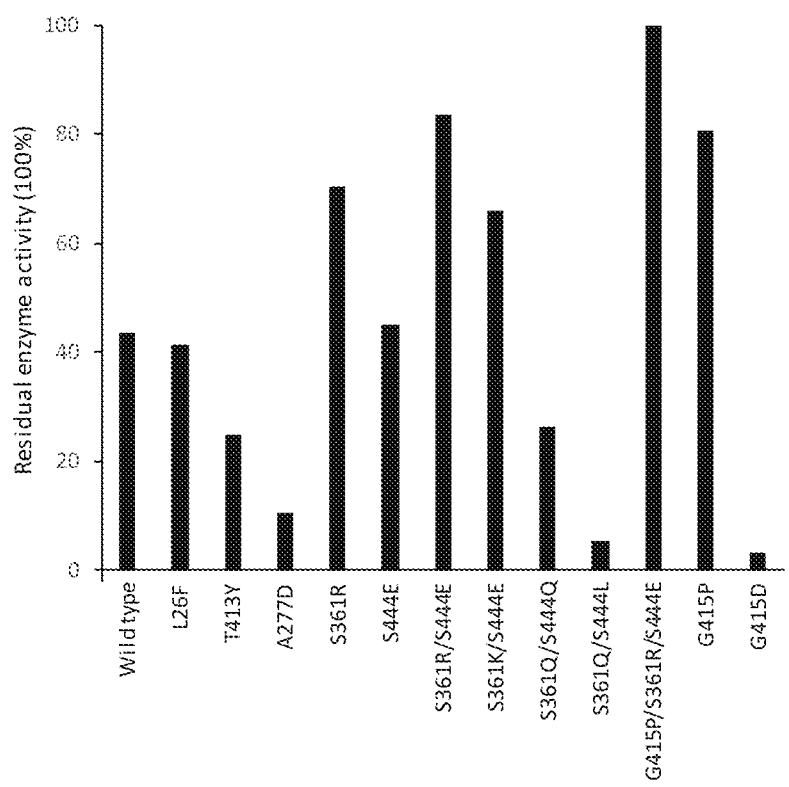
FIG. 1: Residual enzyme activity of the wild type, mutants S361R, S444E, S361R/S444E, S361K/S444E, S361Q/S444Q, S361Q/S444L, G415P/S361R/S444E, G415D, L26F, T413Y, A277D and G415P after heat treatment at 60° C. for 10 min.

E. coli BL21 (DE3), E. coli JM109, and expression vectors pET-24a (+) involved in the following examples are purchased from Takara.

Media involved in the following examples are as follows:
LB liquid medium, containing tryptone 10 g/L, yeast extract 5 g/L, and NaCl 10 g/L.
LB solid medium, containing tryptone 10 g/L, yeast extract 5 g/L, NaCl 10 g/L, and agar powder 20 g/L.
LB liquid medium, containing peptone 12 g/L, yeast extract 24 g/L, glycerin 5 g/L, $KH_2PO_4$ 2.31 g/L, and $K_2HPO_4$ 12.54 g/L.

Detection Methods Involved in the Following Examples are as Follows:

Detection Method of Enzyme Activity of Maltooligosyl Trehalose Synthase:

Preheating: 1.9 mL of a maltodextrin solution 0.2% in mass volume concentration (DE 9-13, pH 6.0 phosphate buffer) is taken in a stoppered test tube, and preheated in a 50° C. water bath for 10 min;

Reaction: After preheating, 0.1 mL of a dilution containing maltooligosyl trehalose synthase is added to the maltodextrin solution, the mixture is shaken uniformly, and the reaction is accurately counted for 10 min; after 10 min, 3 mL of DNS is added, uniform shaking is performed, and reaction is stopped; boiling is performed for 7 min for enzyme deactivation, and cooling is performed to obtain a reaction solution;

Measurement: Distilled water is added to the reaction solution, the volume is adjusted to 15 mL, and uniform mixing is performed; the absorbance is measured at a wavelength of 540 nm and the enzyme activity is calculated.

(Definition of enzyme activity: The unit enzyme activity is equivalent to the amount of enzyme required to convert one micromole of glucose per minute to non-reducing sugar.)

Detection Method of Conversion Rate of Trehalose:

The reaction solution is diluted and precipitated, and the content of trehalose is determined by high performance liquid chromatography (HPLC), and the conversion rate is calculated;

wherein conversion rate (%)=mass of trehalose/mass of rice starch 100%;

HPLC detection conditions: mobile phase (acetonitrile:water=80:20); flow rate: 0.8 mL/min, column temperature 40° C., NH2 column (APS-2 HYPERSIL, Thermo Scientific), refractive index detector (RID).

Example 1: Expression of Wild Type Maltooligosyl Trehalose Synthase

The target gene treY (NCBI number: BAB40765.1) encoding the maltooligosyl trehalose synthase with the nucleotide sequence as shown in SEQ ID NO.7 is synthesized by chemical synthesis. The target gene treY is double digested with Hind III and Nde I, ligated with the expression vector pET-24a (+), and transferred into E. coli BL21 (DE3) to obtain treY/pET24a/BL21 (DE3). The treY/pET24a/BL21 (DE3) is inoculated in the LB liquid medium (containing 100 mg/L kanamycin) and cultured at 37° C. for 10 h to obtain a seed solution. The seed solution is inoculated in the TB liquid medium (containing 100 mg/L kanamycin) at an inoculum concentration of 5%. After culturing at 37° C. for 2 h, IPTG (isopropylthio-β-D galactoside) with a final concentration of 0.01 mmol/L is added for performing induction, and the mixture is fermented at 25° C. on a shaker for 24 h to obtain a fermentation broth. The fermentation broth is centrifuged at 4° C. and 12000 rpm for 10 min, the supernatant is discarded, and the bacteria are collected. The bacteria are resuspended in a 20 mmol/L phosphate buffer (pH 6.0) and the suspension is uniformly mixed. The cell walls of the bacterial suspension are disrupted by an ultrasonic cell disruptor, then the bacterial suspension is centrifuged at 4° C. and 12000 rpm for 10 min, and the supernatant is collected to obtain a fermented intracellular crude enzyme solution;

Wherein, the working conditions of the ultrasonic cell disruptor is: a ψ6 working probe is used, the working time is 10 min, working is performed for 2 s every 3 s, and the working power is 20%.

Example 2: Preparation and Expression of Maltooligosyl Trehalose Synthase Mutant (1) Construction of mutants S361R, S444E, S361R/S444E, S361K/S444E, S361Q/S444Q, S361Q/S444L, G415P/S361R/S444E, G415D, L26F, T413Y, A277D and G415P:

Site-directed mutation is carried out using a treY/pET-24a (+) plasmid as a template by PCR technology;
wherein, mutation primers are:

```
S361R:
                            (SEQ ID NO. 8)
S361R-F: CTGCTGCTCTGCGCGTGTATCGTAGCTACTTACC;

(SEQ ID NO. 9)
S361R-R: GGTAAGTAGCTACGATACACGCGCAGAGCAGCAG;

S444E:
                            (SEQ ID NO. 10)
S444E-F: GCGGTGACCCTGAACTGTTTGCAATCGATGC;

(SEQ ID NO. 11)
S444E-R: GCATCGATTGCAAACAGTTCAGGGTCACCGC;

S361R/S444E (further mutation based on S361R):
                            (SEQ ID NO. 10)
S444E-F: GCGGTGACCCTGAACTGTTTGCAATCGATGC;

(SEQ ID NO. 11)
S444E-R: GCATCGATTGCAAACAGTTCAGGGTCACCGC;

S361K/S444E (further mutation based on S444E):
                            (SEQ ID NO. 12)
S361K-F: TGCTCTGAAAGTGTATCGTAGCTACTTACCAT;

(SEQ ID NO. 13)
S361K-R: ACACTTTCAGAGCAGCAGCAATTTCCA;

S361Q/S444Q (acquisition of S361Q first, and
then further mutation based on S361Q):
                            (SEQ ID NO. 14)
S361Q-F: GCTCTGCAAGTGTATCGTAGCTACTTACCA;

(SEQ ID NO. 15)
S361Q-R: CACTTGCAGAGCAGCAGCAATTTCCA;

(SEQ ID NO. 16)
S444Q-F: GACCCTCAACTGTTTGCAATCGATGCTGC;

(SEQ ID NO. 17)
S444Q-R: ACAGTTGAGGGTCACCGCCCACTTC;
```

-continued

S361Q/S444L (acquisition of S361Q first, and
then further mutation based on 5361Q):
(SEQ ID NO. 18)
S5444L-F: CCTTTACTGTTTGCAATCGATGCTGC;

(SEQ ID NO.19)
S444L-R: GCAAACAGTAAAGGGTCACCGCCCAC;

G415P/S361R/S444E (further mutation based on
S361R/S444E):
(SEQ ID NO. 20)
G415P-F: CAGCAGACCTCACCGATGATCATGGCCAAAGGTGTG;

(SEQ ID NO. 21)
G415P-R: CACACCTTTGGCCATGATCATCGGTGAGGTCTGCTG;

G415D:
(SEQ ID NO. 22)
G415D-F: CTTTCAGCAGACCTCAGATATGATCATGGC;

(SEQ ID NO. 23)
G415D-R: GCCATGATCATATCTGAGGTCTGCTGAAAG;

L26 F:
(SEQ ID NO. 24)
L26F-F: CAGCCCGTATTGTTCCATATTTTCATCGTTTAGGC;

(SEQ ID NO. 25)
L26F-R: GCCTAAACGATGAAAATATGGAACAATACGGGCTG;

T413Y:
(SEQ ID NO. 26)
T413Y-F: CGCTTTCAGCAGTACTCAGGTATGATCATGGCC;

(SEQ ID NO. 27)
T413Y-F: GGCCATGATCATACCTGAGTACTGCTGAAAGCG;

A277D:
(SEQ ID NO. 28)
A277D-F: CACCTCAGTGGCCAATTGATGGTACAACCGG;

(SEQ ID NO. 29)
A277D-R: CCGGTTGTACCATCAATTGGCCACTGAGGTG;

G415P:
(SEQ ID NO. 31)
G415P-F: GCTTTCAGCAGACCTCACCGATGATCATGGC;

(SEQ ID NO. 32)
G415P-R: GCCATGATCATCGGTGAGGTCTGCTGAAAGC;

A PCR system consists of: 0.5 μL of 20 μM forward primer, 0.5 μL of 20 μM reverse primer, 4 μL of dNTPMix, 10 μL of 5×PS Buffer, 0.5 μL of 2.5 U/μL PrimeStar polymerase, 0.5 μL of template, and the balance of double distilled water to 50 μL;

PCR conditions are: Pre-denaturation at 94° C. for 4 min, followed by 25 cycles (at 94° C. for 10 s, at 55° C. for 5 s, at 72° C. for 7 min 40 s) at 72° C. for 10 min, and finally, insulation at 4° C.

The PCR product is detected by 1% agarose gel electrophoresis. After detection, the correct PCR product is digested with Dpn I and transferred to E. coli JM109 competent cells. The transformed product is applied to the LB solid medium containing 100 mg/L of kanamycin and cultured at 37° C. for 12 h. 2 single grown colonies are picked and inoculated into the LB liquid medium, and cultured at 37° C. for 8 h, and then the plasmids are extracted and sequenced. The results are correct and transferred to E. coli BL21 (DE3) to obtain treY/pET24a/BL21 (DE3) after different mutations.

(2) Expression of Mutants

The treY/pET24a/BL21 (DE3) obtained in (1) is inoculated in the LB liquid medium (containing 100 mg/L kanamycin) and cultured at 37° C. for 10 h to obtain a seed solution. The seed solution is inoculated in the TB liquid medium (containing 100 mg/L kanamycin) at an inoculum concentration of 5%. After culturing at 37° C. for 2 h, IPTG (isopropylthio-β-D galactoside) with a final concentration of 0.01 mmol/L is added for performing induction, and the mixture is fermented at 25° C. on a shaker for 24 h to obtain a fermentation broth. The fermentation broth is centrifuged at 4° C. and 12000 rpm for 10 min, the supernatant is discarded, and the bacteria are collected. The bacteria are resuspended in a 20 mmol/L phosphate buffer (pH 6.0) and the suspension is uniformly mixed. The cell walls of the bacterial suspension are disrupted by an ultrasonic cell disruptor, then the bacterial suspension is centrifuged at 4° C. and 12000 rpm for 10 min, and the supernatant is collected to obtain a fermented intracellular crude enzyme solution;

Wherein, the working conditions of the ultrasonic cell disruptor is: a ψ6 working probe is used, the working time is 10 min, working is performed for 2 s every 3 s, and the working power is 20%.

Example 3: Detection of Residual Enzyme Activity of Maltooligosyl Trehalose Synthase after Heat Treatment The fermented intracellular crude enzyme solution obtained in Example 1 is purified to obtain a pure enzyme, and the pure enzyme is the wild type. The fermented intracellular crude enzyme solutions obtained in Example 2 are purified to obtain pure enzymes, and the pure enzymes are respectively S361R, S444E, S361R/S444E, S361K/S444E, S361Q/S444Q, S361Q/S444L, G415P/S361R/S444E, G415D, L26F, T413Y, A277D and G415P.

The wild type, S361R, S444E, S361R/S444E, S361K/S444E, S361Q/S444Q, S361Q/S444L, G415P/S361R/S444E, G415D, L26F, T413Y, A277D and G415P are diluted with a 20 mM pH 6.0 phosphate buffer solution respectively until the protein concentration is 0.25 mg/mL. The enzyme activity of the dilutions containing the wild type, S361R, S444E, S361R/S444E, S361K/S444E, S361Q/S444Q, S361Q/S444L, G415P/S361R/S444E, G415D, L26F, T413Y, A277D and G415P is detected. The detection results are: the enzyme activity of the dilution containing the wild type is 200 U/mL, the enzyme activity of the dilution containing the S361R is 196 U/mL, the enzyme activity of the dilution containing the S444E is 187 U/mL, the enzyme activity of the dilution containing the S361R/S444E is 210 U/mL, the enzyme activity of the dilution containing the S361K/S444E is 203 U/mL, the enzyme activity of the dilution containing the S361Q/S444Q is 190 U/mL, the enzyme activity of the dilution containing the S361Q/S444L is 192 U/mL, the enzyme activity of the dilution containing the G415P/S361R/S444E is 198 U/mL, the enzyme activity of the dilution containing the G415D is 124 U/mL, the enzyme activity of the dilution containing the L26F is 203 U/mL, the enzyme activity of the dilution containing the T413Y is 200 U/mL, the enzyme activity of the dilution containing the A277D is 209 U/mL, and the enzyme activity of the dilution containing the G415P is 180 U/mL.

The wild type, S361R, S444E, S361R/S444E, S361K/S444E, S361Q/S444Q, S361Q/S444L, G415P/S361R/S444E, G415D, L26F, T413Y, A277D and G415P are diluted with a 20 mM pH 6.0 phosphate buffer solution respectively until the protein concentration is 0.25 mg/mL. The obtained diluents are subjected to heat treatment in 60° C. thermostatic waterbath for 10 min. After 10 min, the enzyme activity of the dilutions containing the wild type, S361R, S444E, S361R/S444E, S361K/S444E, S361Q/

S444Q, S361Q/S444L, G415P/S361R/S444E and G415P not subjected to the heat treatment is taken as 100%, the residual enzyme activity of the dilutions containing the wild type, S361R, S444E, S361R/S444E, S361K/S444E, S361Q/S444Q, S361Q/S444L, G415P/S361R/S444E, G415D, L26F, T413Y, A277D and G415P subjected to the heat treatment is detected, and the detection results are shown in FIG. 1.

Seen from FIG. 1, in all the mutants, the residual enzyme activity of only the mutants S361R, S444E, S361R/S444E, S361/S444E, G415P/S361R/S444E and G415P is improved as compared with the wild type, and the residual enzyme activity of the other mutants is lower than that of the wild type, wherein the residual enzyme activity of the mutant S361R is 70.3%, the residual enzyme activity of the S444E is 50.1%, the residual enzyme activity of the S361R/S444E is 83.5%, the residual enzyme activity of the S361K/S444E is 65.9%, the residual enzyme activity of the G415P/S361R/S444E is 100%, the residual enzyme activity of the G415P is about 80.7%, which are respectively 1.6 times, 1.1 times, 1.9 times, 1.5 times, 2.3 times and 1.9 times of that of the wild type.

Example 4: Analysis of Thermal Stability of Maltooligosyl Trehalose Synthase The dilutions containing the wild type, G415D and G415P obtained in Example 3 are placed in a 50° C. thermostatic waterbath, and sampled once at set intervals to detect the residual enzyme activity and compare the thermal stability, and the detection results are shown in FIG. 2.

Figure 2:
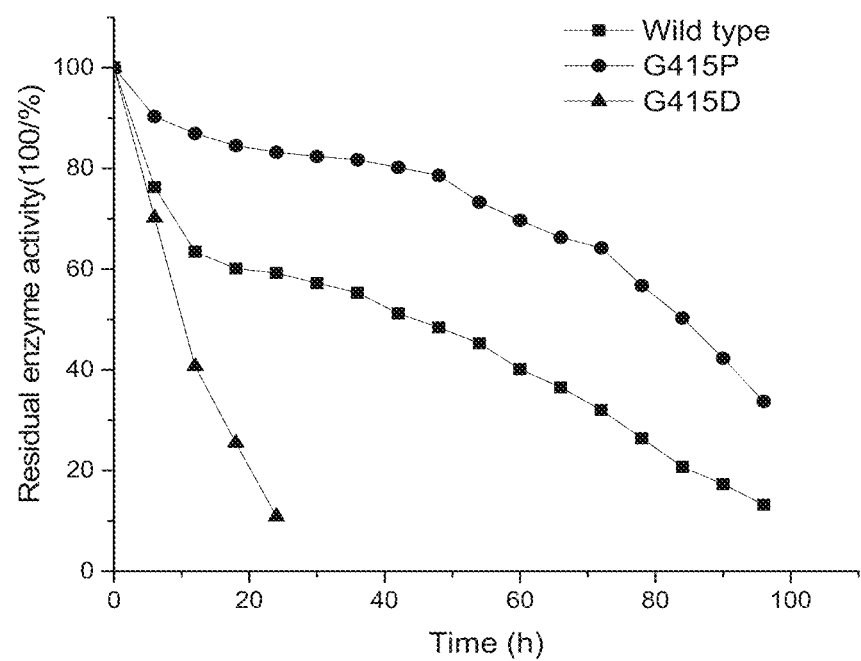
FIG. 2: Thermal stability of the wild type, mutant G415P and mutant G415D at 50° C.

See from FIG. 2, the half-life of the mutant G415P at 50° C. is 41 h longer than that of the wild type, and is twice of that of the wild type, indicating that the thermal stability of the mutant G415P is significantly improved. The half-life of the mutant G415D at 50° C. is 32 h shorter than that of the wild type, and is 25% of that of the wild type, indicating that the thermal stability of the mutant G415D is significantly reduced.

Figure 3:
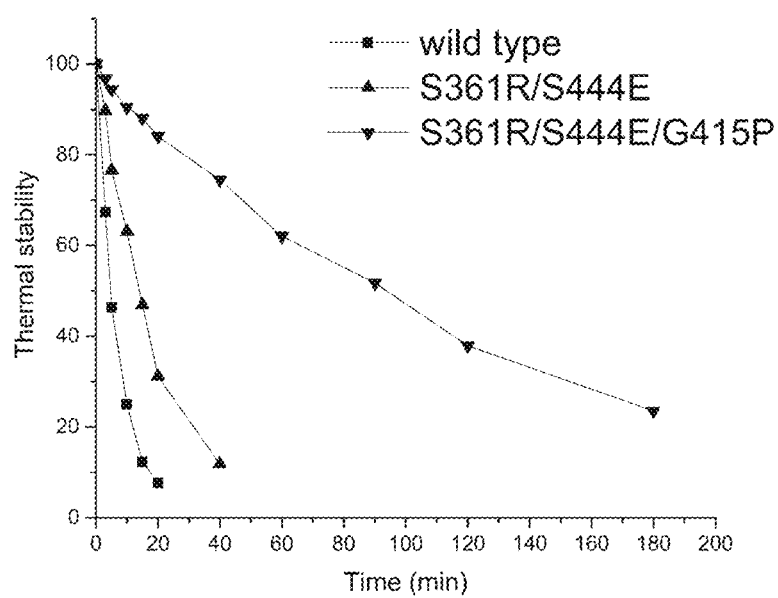
FIG. 3: Thermal stability of the wild type, mutant S361R/S444E and mutant G415P/S361R/S444E at 60° C.

The dilutions containing the wild type, S361R/S444E and G415P/S361R/S444E obtained in Example 3 are placed in a 60° C. thermostatic waterbath, and sampled once at set intervals to detect the residual enzyme activity and compare the thermal stability, and the detection results are shown in FIG. 3.

Seen from FIG. 3, the half-lives of the mutants S361R/S444E and G415P/S361R/S444E at 60° C. are respectively prolonged by 10.3 min and 86.2 min than that of the wild type, which are 3.2 times and 19.7 times of that of the wild type, indicating that the thermal stability of the mutants S361R/S444E and G415P/S361R/S444E is significantly improved.

Example 5: Analysis of Conversion Rate of Maltooligosyl Trehalose Synthase to Trehalose A rice starch solution with a concentration of 150 g/L is used as a substrate, 0.5 U/mL α-amylase (Termamyl SC, purchased from Novozymes) is added to the rice starch solution, the mixture is liquefied at pH 5.5 and temperature of 90° C. for 8-10 min until a DE value is 16 to obtain an enzymatic hydrolysate. After the temperature of the enzymatic hydrolysate reduces to 60° C., 5 U/g starch pullulanase (derived from *Bacillus deramificans*), 2 U/mL cyclodextrin glucosyltransferase (derived from *Paenibacillus macerans*), 0.5 U/mL 4-α glycosyltransferase (derived from *Thermus aquaticus*), 5.0 U/mL maltooligosyl trehalose hydrolase (derived from *A. ramosus*) and the wild type or the mutant G415P with the gradient concentrations of 1.5 U/mL, 2.0 U/mL, 2.5 U/mL and 3.0 U/mL obtained in Example 3 are added to the enzymatic hydrolysate. The mixture reacts at 50° C. and 150 r/min for 36 h to obtain a reaction solution. The reaction solution is boiled for stopping the reaction to detect the conversion rate of the trehalose, and the detection results are shown in FIG. 4.

Figure 4:
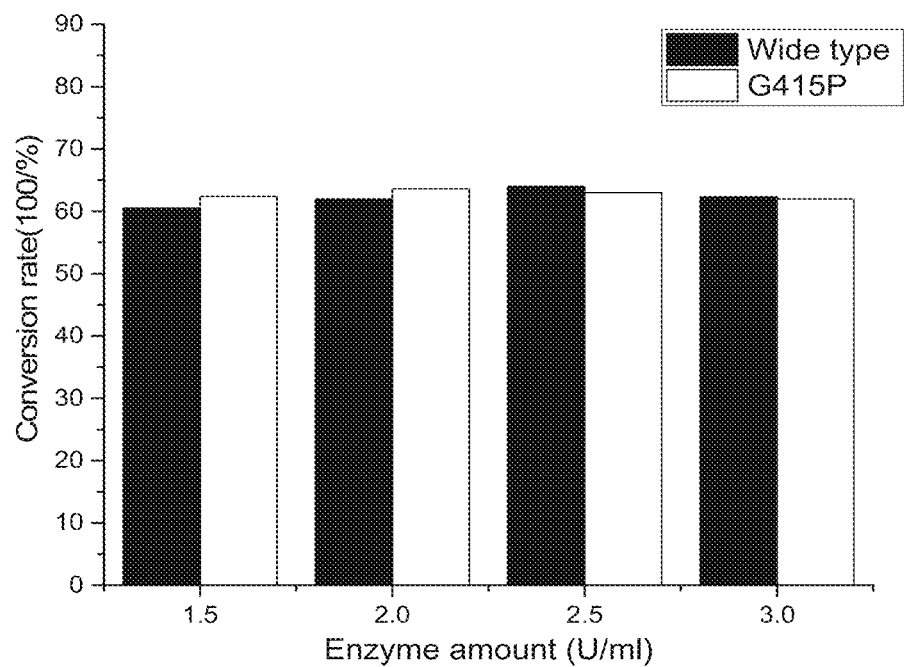
FIG. 4: Conversion rates of the wild type and mutant G415P for producing trehalose at 60° C.

Seen from FIG. 4, the optimal enzyme amount of the wild type is 2.5 U/mL, the optimal enzyme amount of the mutant G415P is 2.0 U/mL, and the enzyme amount of the mutant G415P relatively decreases. At the optimal enzyme amount, the conversion rate of the wild type is 64.0%, and the conversion rate of the mutant is 63.6%, indicating that the mutant G415P has no adverse effect on the conversion rate.

The wild type obtained in Example 3 is used as a control, a rice starch solution with a concentration of 150 g/L is used as a substrate, 0.5 U/mL α-amylase (Termamyl SC, purchased from Novozymes) is added to the rice starch solution, the mixture is liquefied at pH 5.5 and temperature of 90° C. for 8-10 min until a DE value is 16 to obtain an enzymatic hydrolysate. After the temperature of the enzymatic hydrolysate reduces to 60° C., 5 U/g starch pullulanase (derived from *B. deramificans*), 2 U/mL cyclodextrin glucosyltransferase (derived from *P. macerans*), 0.5 U/mL 4-α glycosyltransferase (derived from *T. aquaticus*), 5.0 U/mL maltooligosyl trehalose hydrolase (derived from *A. ramosus*) and 5.0 U/mL mutant G415P/S361R/S444E are added to the enzymatic hydrolysate. The mixture reacts at 60° C. and 150 r/min for 36 h to obtain a reaction solution. The reaction solution is boiled for stopping the reaction to detect the conversion rate of the trehalose, and the detection results are shown in FIG. 5.

Figure 5:
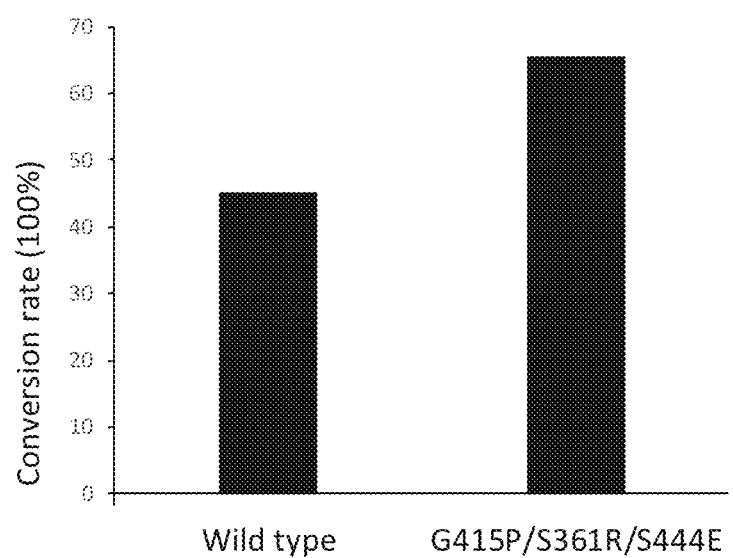
FIG. 5: Conversion rates of the wild type, mutant G415P/S361R/S444E for producing trehalose at 60° C.

Seen from FIG. 5, the conversion rate of the mutant G415P/S361R/S444E for producing trehalose at 60° C. is up to 65.3%, which is improved by 20.2% compared with the wild type, proving that the mutant G415P/S361R/S444E has significantly improved thermal stability, can produce trehalose at higher temperatures, and has a higher conversion rate than that of the wild type.

Although the present disclosure has been disclosed above in the preferred examples, it is not intended to limit the present disclosure. Any person skilled in the art can make various alterations and modifications without departing from the spirit and scope of the present disclosure. Therefore, the scope of the present disclosure should be determined by the scope of the claims.

What is claimed is:

1. A maltooligosyl trehalose synthase mutant, comprising the amino acid sequence SEQ ID NO:1,
   wherein the amino acid sequence additionally comprises a point mutation at:
   (a) 415G,
   (b) 361S,
   (c) 444S,
   (d) 361S and 444S, or
   (e) 415G, 361S, and 444S.

2. A maltooligosyl trehalose synthase mutant, comprising the amino acid sequence SEQ ID NO:1, wherein the amino acid sequence additionally comprises one of the following point mutations:
   (f) G415P,
   (g) S361R,
   (h) S444E,
   (i) S361R and S444E,
   (j) S361K and S444E, or
   (k) S361R, S444E, and G415P.

3. The maltooligosyl trehalose synthase mutant of claim 1, wherein the amino acid sequence of the mutant is SEQ ID NO: 2, SEQ ID NO: 3, SEQ ID NO: 4, SEQ ID NO: 5, SEQ ID NO: 6, or SEQ ID NO: 30.

4. The maltooligosyl trehalose synthase mutant of claim 2, wherein the amino acid sequence of the mutant is SEQ ID NO: 2, SEQ ID NO: 3, SEQ ID NO: 4, SEQ ID NO: 5, SEQ ID NO: 6, or SEQ ID NO: 30.

* * * * *